United States Patent
Ingenito et al.

(10) Patent No.: US 6,653,525 B2
(45) Date of Patent: Nov. 25, 2003

(54) PROSTHETIC DEVICE FOR RESPIRATORY PATIENTS

(75) Inventors: Edward P. Ingenito, Kingston, MA (US); John J. Reilly, Jr., Wellesley, MA (US); Steven J. Mentzer, Boston, MA (US); Scott J. Swanson, Milton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 77 days.

(21) Appl. No.: 10/046,910

(22) Filed: Jan. 17, 2002

(65) Prior Publication Data

US 2002/0165618 A1 Nov. 7, 2002

Related U.S. Application Data

(60) Provisional application No. 60/262,063, filed on Jan. 18, 2001.

(51) Int. Cl.⁷ .............................. A61F 2/02; A61F 2/04; A61M 29/00
(52) U.S. Cl. .............................. 623/11; 623/12; 606/192
(58) Field of Search .............................. 623/7, 8, 9, 11, 623/12; 606/192

(56) References Cited

U.S. PATENT DOCUMENTS

| | | | | |
|---|---|---|---|---|
| 3,650,268 A | * | 3/1972 | Ruben ..................... | 128/145.7 |
| 4,219,026 A | * | 8/1980 | Layton ..................... | 128/325 |
| 4,685,446 A | * | 8/1987 | Choy ..................... | 128/1 D |
| 4,800,901 A | * | 1/1989 | Rosenberg ..................... | 128/899 |
| 4,969,899 A | * | 11/1990 | Cox ..................... | 623/8 |
| 5,056,505 A | * | 10/1991 | Warwick et al. ............. | 128/30.2 |
| 5,146,933 A | * | 9/1992 | Boyd ..................... | 128/899 |
| 5,578,085 A | * | 11/1996 | Johnson, Jr. et al. ......... | 623/11 |
| 5,700,269 A | * | 12/1997 | Pinchuk et al. .............. | 606/108 |
| 5,800,528 A | | 9/1998 | Lederman et al. ............. | 623/3 |
| 5,827,289 A | * | 10/1998 | Reiley et al. ................ | 606/86 |
| 6,264,667 B1 | * | 7/2001 | McGuckin, Jr. ............ | 606/167 |
| 6,391,060 B1 | | 5/2002 | Ory et al. ................ | 623/23.76 |

FOREIGN PATENT DOCUMENTS

| | | | | |
|---|---|---|---|---|
| FR | 2 769 825 | | 5/2002 | ............. A61F/2/02 |
| WO | WO 93/10723 | * | 6/1993 | ............. A61F/2/02 |
| WO | WO 98/55165 | | 12/1998 | ............. A61M/1/12 |
| WO | WO 00/36995 | | 6/2000 | ............. A61F/2/00 |

OTHER PUBLICATIONS

Brenner, et al., "Rate of $FEV_1$ Change Following Lung Volume Reduction Surgery," Chest 113:652–659 (1998).
Cooper, et al., "Bilateral Pneumectomy (Volume Reduction) for Chronic Obstructive Pulmonary Disease," J. Thorac. Cardiovasc. Surg. 109:106–109 (1995).
Feinleb, et al., "Trends in COPD Morbidity and Mortality in the United States," Am. Rev. Respir. Dis. 140:S9–S18 (1989).
Fessler, et al., "Lung Volume Reduction Surgery and Airflow Limitation," Am. J. Respir. Crit. Care Med. 157:715–722 (1998).
Ingenito, et al., "Relation Between Preoperative Inspiratory Lung Resistance and the Outcome of Lung–Volume–Reduction Surgery for Emphysema," N. Eng. J. Med. 338:1181–1185 (1998).
Martinez, et al., "Lung–Volume Reduction Improves Dyspnea, Dynamic Hyperinflation, and Respiratory Muscle Function," Am. J. Respir. Crit. Care Med. 155:1984–1990 (1997).

* cited by examiner

Primary Examiner—Michael J. Milano
Assistant Examiner—Charles H. Sam
(74) Attorney, Agent, or Firm—Michael A. Sanzo; Fitch, Even, Tabin & Flannery

(57) ABSTRACT

The present invention is directed to a prosthetic device that can be implanted in the pleural cavity of patients undergoing lung volume reduction surgery. The device is designed so that its volume can be adjusted by externally adding or removing gas without the need for additional surgical intervention.

11 Claims, 5 Drawing Sheets

PROSTHETIC DEVICE FOR RESPIRATORY PATIENTS

CROSS REFERENCE TO RELATED APPLICATIONS

The present application claims the benefit of U.S. provisional application No. 60/262,063, filed on Jan. 18, 2001.

FIELD OF THE INVENTION

The present invention is directed to a prosthetic device that can be surgically implanted between the chest wall and lungs of a patient. The device has a bladder with a volume that can be adjusted by externally inserting or removing gas and is of particular use for emphysema patients that have undergone lung volume reduction surgery. In addition, the device can be used to provide respiratory support for patients.

BACKGROUND OF THE INVENTION

Emphysema is a disabling disease that causes progressive and irreversible damage to lung tissue. It is the forth leading cause of death in the United States and a major cause of morbidity and mortality worldwide (Feinlieb, et al., *Am. Rev. Respir. Dis.* 140:s9–s18 (1989)). In its purest form, emphysema affects between 1.5 and 2 million Americans. However, the vast majority of the 12 million people in this country with disabling chronic obstructive pulmonary disease, including those with diagnoses of chronic bronchitis and asthma, also have a major component of disease related to emphysema. Thus, it is estimated that emphysema contributes to lung dysfunction in 6–8 million people in the U.S., and in many more individuals worldwide (Higgins, et al., in *Clinical Epidemiology of Chronic Obstructive Pulmonary Disease*, pp. 23–43, Marcel Dekker, New York).

It has been recently shown that respiratory function in emphysema patients can be improved by surgically resecting the most badly damaged regions of tissue (Cooper, et al., *J Thorac. Cardiovasc. Surg.* 109:106–119 (1995)). The technique, termed "lung volume reduction surgery" (LVRS), has become a preferred therapeutic option in patients with end stage disease (Ingenito, et al., *N. Encl. J Med.* 338:1181–1185 (1998); Martinez, et al., *Am. J Resp. Crit. Care Med.* 157:A497 (1998)). Unfortunately, the benefits derived from LVRS vary significantly from patient to patient and are lost over time. If a means can be found for post-operatively adjusting effective lung size without a need for further surgery, then LVRS could be performed more effectively and more safely in most patients and the long term benefits of LVRS should be greatly improved.

SUMMARY OF THE INVENTION

The present invention is based upon the development of a prosthetic device that can be implanted into the pleural cavity of patients for the purpose of improving respiratory function. The main characteristic of the device is that its volume can be adjusted through a subcutaneous port to improve the recoil of lung tissue and to thereby optimize the physiological benefits derived from lung volume reduction surgery.

In its first aspect, the invention is directed to the implantable prosthetic device itself. The device is comprised of a bladder and an attached connector tube. The bladder is made of material that is biocompatible, impermeable to gas and elastomeric, i.e., it should be non-rigid, and exert recoil pressure upon expansion. The bladder should fit snuggly within the pleural cavity between a patient's lungs and their chest wall and be of a sufficient size to exert inward pressure on the lung when expanded. The outer surface of the device which rests against the chest wall will typically be coated with a lubricating biocompatible hydrogel to allow the chest wall to slide easily across the surface and prevent the formation of adhesions.

The bladder of the device has two chambers: an inner chamber formed by the lumen of multiple septated compartments; and an outer chamber, external to the septated compartments and internal to the inner surface of said bladder. The septated compartments are made of biocompatible gas-impermeable, elastomeric material and are interconnected to allow the exchange of gas. Upon inflation of the inner chamber of the bladder, the device assumes a crescentic shape that generally matches the contour of the pleural cavity. In a preferred embodiment, the bladder has multiple distinct lobes, preferably three, to help it adjust to different lung contours.

The connector tube, also made of biocompatible, elastomeric material that is gas impermeable, provides two separate passageways for gas, one to the inner chamber of the bladder and one to the outer chamber. For the purpose of the present invention, the end of the connector tube attached to the bladder is termed its "distal end." The other, "proximal," end of the connector tube ends in two self-sealable ports, one for the passageway into the inner chamber of the bladder and the other for the passageway into the outer chamber. In a preferred embodiment, each sealable port is designed so that it is compatible with the introduction of gas or fluid using a syringe. The entire device must be suitable for surgical implantation. This means, among other things, that it must be chemically inert, non-immunogenic, and sterile. Preferred materials for constructing the device are silicone rubber, and polymers such as polypropylene and polyurethane. In general, the bladder of the prosthetic device should be 20–40 cm in diameter, each septated compartment should be 1–2 cm in diameter, and the connector tube should be 10–20 cm in length.

The outer chamber of the prosthetic device may also be connected to an oscillating pump to provide a means for reciprocally expanding and contracting the bladder. The pump is maintained outside of a patient's body and is connected to the implanted device by means of a large bore needle inserted into the sealable port on the subcutaneously positioned connector tube. This arrangement is particularly preferred for providing breathing assistance to patients experiencing respiratory failure.

The prosthesis may be used in connection with a rigid deployment device to help in positioning the bladder after passing it through a mini-thoracotomy incision or during video-assisted thoracoscopic surgery. The deployment device has a handle attached to a retractable arm that extends through a surrounding sheath. Movable grasping prongs hold the ends of the bladder and are pivotally attached to the distal end of the retractable arm (i.e., the end that passes into the chest cavity of a patient) by means of a spring loaded hinge. This exerts pressure on the movable prongs, pushing them in an outward direction. At the end of the retractable arm opposite to the handle, there is a rounded cap that helps the device smoothly pass through a surgical incision. The sheath compresses the movable grasping prongs when the retractable arm is in its normal, retracted position. In order to open the prongs and thereby spread the bladder, the retractable arm is pushed through the sheath to an extended position in which the spring loaded hinge is outside the end of the sheath. As with the prosthesis, the deployment devise is constructed of material suitable for surgical use.

In another aspect, the invention is directed to a method of treating a patient for emphysema or respiratory failure by surgically implanting the prosthetic device described above. The bladder is positioned in the patient's pleural cavity and the ports on the connector tube are positioned either at the surface of the patient's skin or immediately under the skin. The ports provide a means for externally adjusting the volume occupied by the bladder within the patient's pleural cavity. In a preferred embodiment, the device is implanted in emphysema patients that have undergone lung volume reduction surgery. Post-operatively, gas may be introduced or removed from the bladder in order to optimize the lung recoil of the patient. Thus, adjustments can be made in response to disease progression without the need for additional surgery. When used in this manner gas should be added to or removed from the septated inner chamber of the bladder.

In a preferred embodiment of the method, the prosthetic device is directly attached to the visceral pleural surface of a patient's lung. Attachment of this nature helps to reduce air leaks that sometimes occur in patients that have undergone lung volume reduction surgery. Bonding is accomplished by coating the visceral pleural surface of the lung with thrombin and coating the surface of the prosthetic device that will contact the lung with a fibrinogen or a fibrin/collagen mixture. When the thrombin-coated lung surface makes contact with the fibrinogen-coated surface of the prosthetic device, a fibrin matrix is formed that holds the two surfaces together.

In addition, the present invention encompasses a method for providing respiratory assistance to a patient by surgically implanting the prosthetic device described above and then attaching it to an oscillating pump. In this embodiment, gas is cyclically pumped into and out of the non-septated outer bladder chamber. The pump is used to alternately inflate and deflate the bladder in order to support the patient's breathing. Once a patient recovers to the point where assisted respiration is no longer needed, the device can be either removed or left in place after positioning the sealable ports for easy external access. In this manner, long term control over lung recoil can be achieved.

BRIEF DESCRIPTION OF THE FIGURES

FIG. 1 depicts two versions of the prosthetic device of the present invention in a deflated state. In FIG. 1a, a device is shown in a view looking down from about a 45 degree angle. The reference numerals refer to the following structures: 1, outer surface of the bladder wall; 2, attachment between distal end of the connector tube and the bladder; 3, dual connector tube; and 4, proximal end of connector tube with dual self sealing ports. The preferred device is shown in a top view in FIG. 1b. In this, the bladder has a multi-lobed, "butterfly," arrangement that maximizes its ability to conform to different chest and lung configurations. The bladder should ordinarily be 20 to 40 cm in diameter.

FIG. 2 is a top view of the prosthetic device of FIG. 1b in which the lower left lobe is in cross-section to show the dual chambers within the bladder. The bladder contains numerous, inflatable septated compartments (reference numeral 5) with interconnections (6) that allow for the passage of gas. Each individual septated compartment is, preferably, between 1 and 2 cm in diameter and is made of elastomeric, gas impermeable material. The lumen of the network of septa together form the inner chamber of the bladder (8). The bladder also has an outer chamber (7) which is external to the septated compartments and internal to the inner surface of the bladder wall. Each chamber within the bladder is connected to a separate port for inflation.

FIG. 3 is crossectional side view of the prosthetic device. It can be seen that the connector tube is divided into two separate passageways for gas. One passageway (9) allows for the inflation of the inner chamber (8) through a first port (11). Gas is exchanged between septated compartments (5) through interconnecting openings (6). The second passageway (10) allows for the inflation of the outer chamber of the bladder (7) through a second port (12). Each of the ports end in a self-sealing membrane (13) that may be perforated with a syringe needle.

FIG. 4 shows two top crossectional views of the prosthetic device in use. In FIG. 4a, the bladder of the device has made contact with the lung of a patient that has undergone LVRS. Surgical staplelines are shown as reference numeral 14. For this type of patient, adjustments in the pressure exerted by the bladder will be made primarily using the inner chamber of the device (8). Gas will be introduced or removed through the passageway (9) and port (11) that lead to this chamber. The septations will help to provide uniform, equally distributed pressure to the lung. FIG. 4b is intended to represent the device being used to provide ventilator support to a patient. Under these circumstances gas will be alternately introduced and removed from the outer chamber of the bladder (7) by means of an oscillating gas pump attached to the outer chamber passageway (10). A relatively large bore port (12 in FIG. 4a) should be used to allow for rapid gas exchange.

FIG. 5 shows a deployment device that may be used to help in positioning the prosthetic device during surgery. This device has a handle (15) attached to an retractable arm with a ratchet-toothed region (16). The retractable arm ends in a fixed (i.e., nonmovable) prong (18) and has movable grasping prongs (19) that are pivotally attached to the arm by means of a spring loaded hinge (22) exerting pressure on the movable prongs in an outward direction from the fixed prong. The fixed prong is attached to a rounded cap (20) that may be pushed through a surgical opening into the chest cavity of a patient. Prior to surgery, the movable grasping prongs are attached to the bladder of the prosthetic device, e.g., each prong may grasp the end of the lobe of a bladder, and are held in a contracted state by means of an outer sheath (21) which surrounds the arm. The arm is held in place within the sheath by means of a positioning gasket (23). A moveable release lever (17) is pivotally attached to the sheath and engages the ratchet teeth of the arm. When pressure is applied to the release lever, it disengages from the ratchet teeth, permitting the arm to be pushed through the sheath.

FIG. 6 is a crossectional view through the sheath (21) of the deployment device at the position of the release lever (17). The figure shows the arm of the device (16) and the positioning gasket (23).

FIG. 7a shows the handle (15), arm (16), fixed prong (18), movable grasping prongs (19), cap (20), and spring loaded hinge (22) of the deployment device. FIG. 7b shows the movable grasping prongs (19) in the fully open they would assume when they are extended beyond the end of the sheath (FIG. 5, reference numeral 21).

DETAILED DESCRIPTION OF THE INVENTION

Figure 1A:
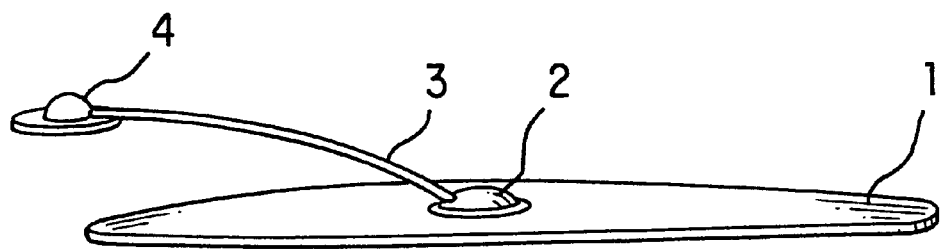
FIGS. 1a–1b.

The present invention is directed to a prosthetic device and to the use of this device in the treatment of respiratory patients, particularly emphysema patients and patients in respiratory failure. The general features of the prosthesis can be seen in FIGS. 1–4. The device has a bladder (reference numeral 1) with an inner network of expandable, gas impermeable septated compartments (5). The septated compartments (each about 1–1.5 cm in diameter) are interconnected (6) by openings that allow for the exchange of gas which may be externally introduced or removed through a passageway (9) in a connector tube (3). The passageway ends in a port (11) that is covered with self sealing septum (13) that allows for the introduction or removal of gas by means of a syringe. Thus, the interconnected septated compartments together form an expandable chamber (8) that push against the bladder wall to exert pressure on a patient's lung.

The bladder of the prosthesis also has a second, "outer," chamber (7) formed by the area outside of the septated compartments but inside the inner wall of the bladder. This is connected to a second passageway (10) through the connector tube (3). The second passageway ends in a second port (12) covered with a self sealing septum (13) and this provides an alternative means for expanding the bladder.

Figure 1B:
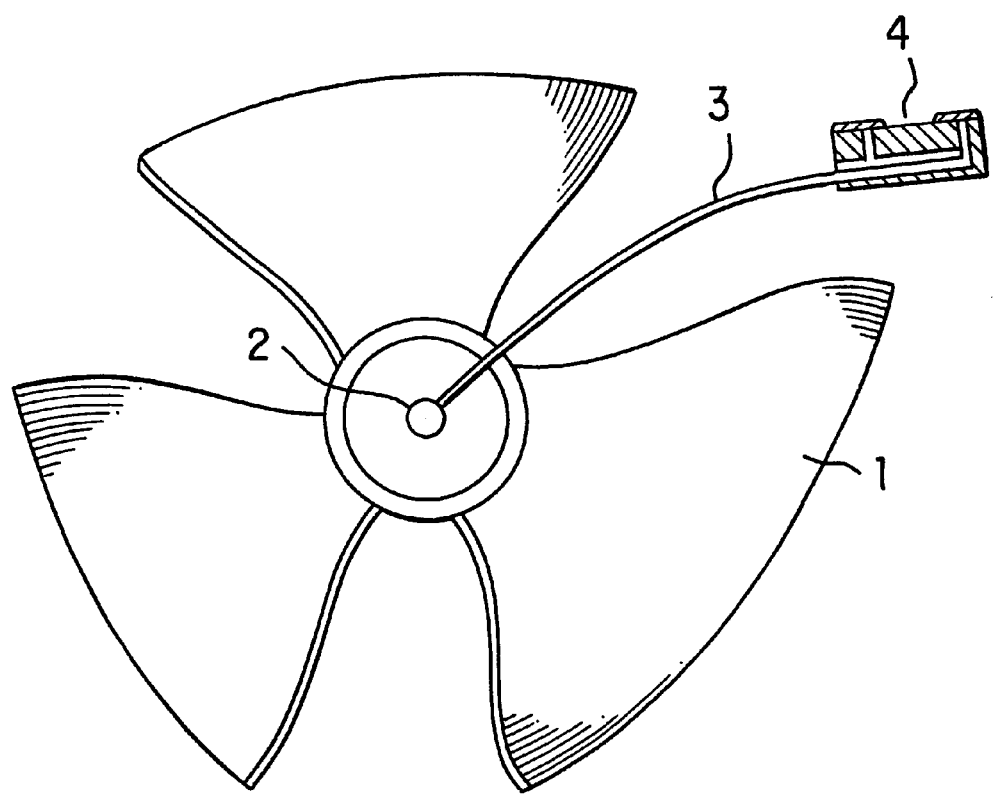
Figure 2:
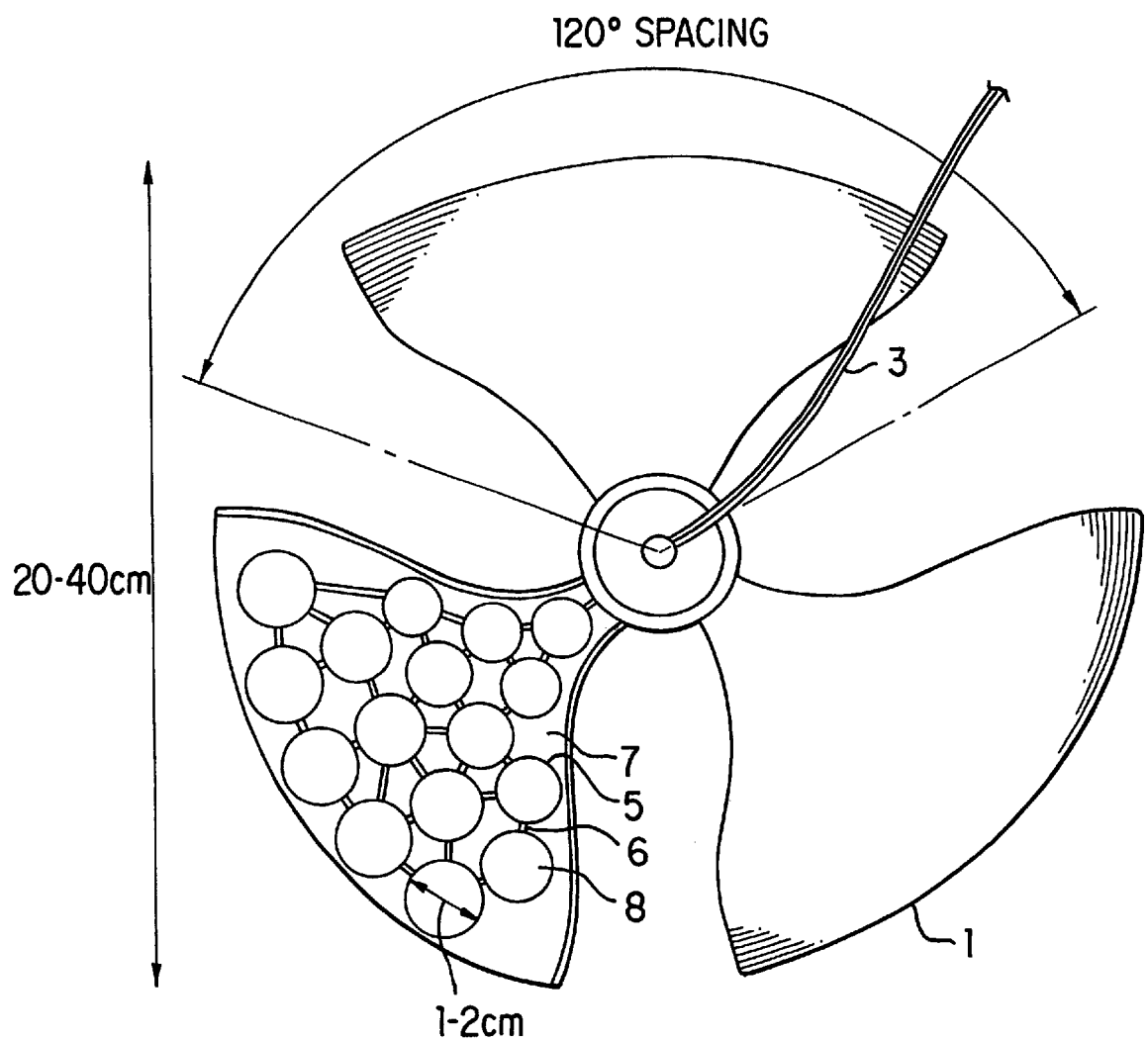
FIG. 2.
Figure 3:
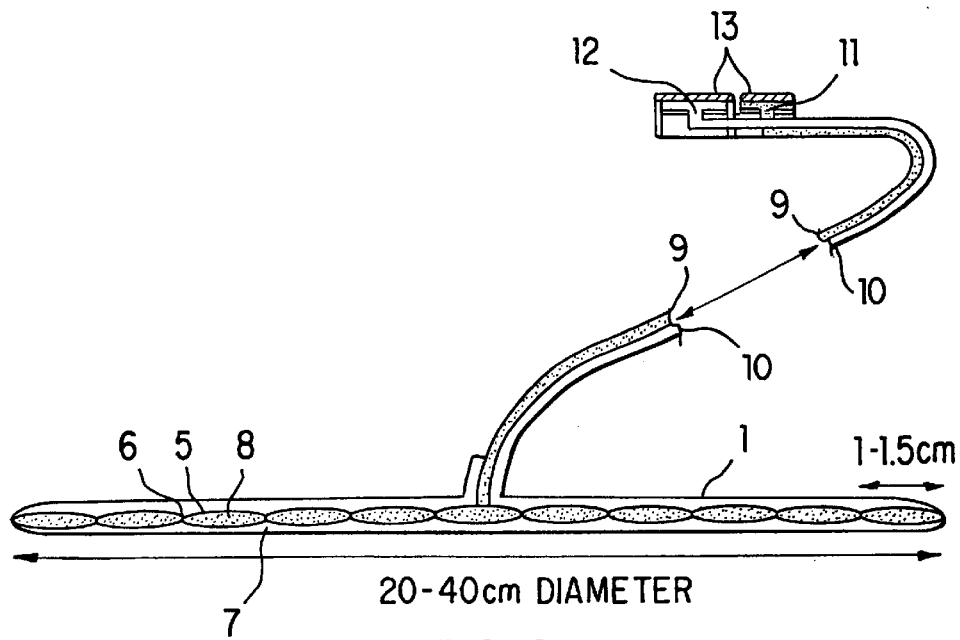
FIG. 3.

The bladder should be of a size that corresponds to the pleural cavity of the patient and can be manufactured using standard techniques well-known in the art. Although not essential, the size of the bladder can be customized for use in a particular patient using methods such as those described in U.S. Pat. No. 5,578,085. Depending upon clinical factors, the bladder may be designed to cover the portion of the pleural cavity occupied by a single lung or it may be designed to cover the entire cavity. In the most preferred embodiment, the device has a bladder that is divided into multiple lobes (FIG. 1b). This allows the bladder to adapt to different chest configurations and maintain good contact with a patient's lung.

A dual lumen connector tube (reference numeral 3) has a distal end that forms an attachment with the bladder (reference numeral 2) and provides two separate passageways, one to the inner chamber of the bladder and the other to the outer chamber of the bladder. Although, in FIGS. 1 and 2, the connector tube is shown as forming an attachment near the center of the bladder, other sites for attachment may also be used. It is generally preferred that the connector tube be attached by molding it directly to the inner portion of the bladder, although other types of connections may be used provided that they are secure and air tight. Both the connector tube and the bladder should be made of material that is biocompatible, essentially gas impermeable, and elastomeric. Preferred materials include silicone rubber such as Silastic™, and polymers such as polypropylene. The use of such materials in prosthetic implants and techniques for molding such materials into desired shapes are well-known in the art.

The connector tube is 10–20 cm in length and is attached to sealable ports (reference numerals 11 and 12) which provide a means for introducing gas into the device. The ports may be made of a biocompatible polymer that is more rigid than the connector tube or bladder. Any of the surgically implantable sealable ports known in the art are suitable for use in the device provided that they are gas impermeable. Particularly preferred are ports that are designed to be accessed by means of a syringe.

Figure 4A:
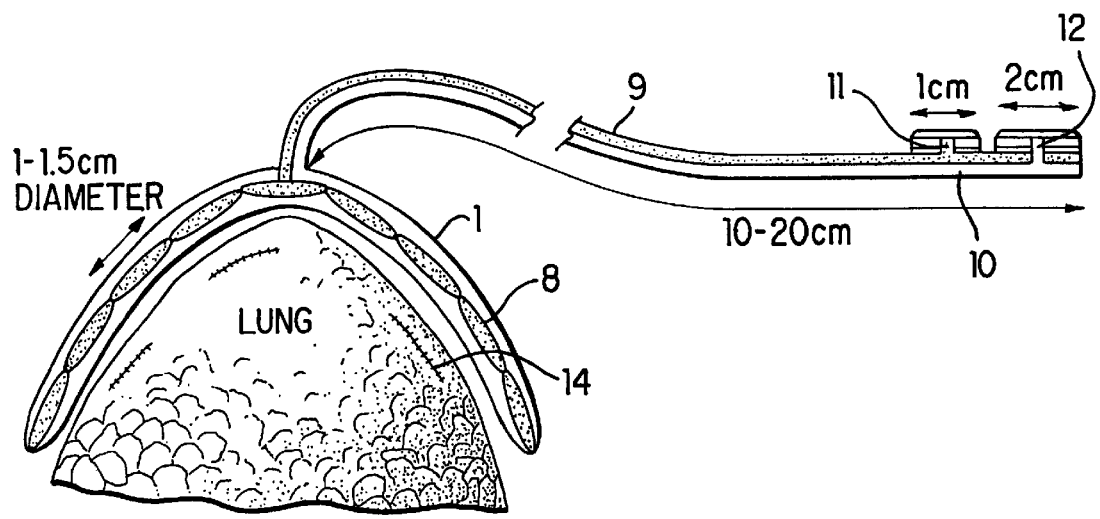
FIGS. 4a–4b.

FIG. 4a depicts the prosthetic device after implantation in a patient that has undergone LVRS. When used in this manner, the pressure that the device exerts on the patient's lung is adjusted by expanding or contracting the inner chamber (8) of the bladder. In order to exert more pressure, gas is injected through the port (11) connected to the inner chamber passageway (9). When this occurs, one side of the bladder pushes against the chest wall of the patient and the opposite side pushes against the patient's lung.

Figure 4B:
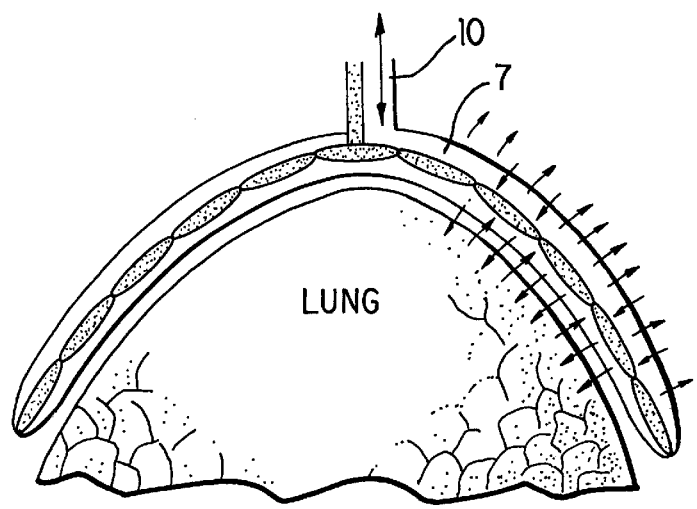

The prosthesis may also be used as a ventilator support device (FIG. 4b). Under these circumstances, an oscillating pump is connected to the port (12) of the outer chamber passageway (10). Pressure is then alternately applied and released to the patent's lung by expanding and contracting the outer chamber. Upon expansion, the walls of the bladder naturally vibrate thereby improving gas mixing. The reciprocal expansion and contraction of the bladder should occur in a rhythm appropriate for supporting the patient's breathing. Frequency ranges for reciprocal expansion and contraction include those corresponding to conventional ventilation, as well as those employed during high frequency ventilation (0–1000 cycles/min.).

Figure 5:
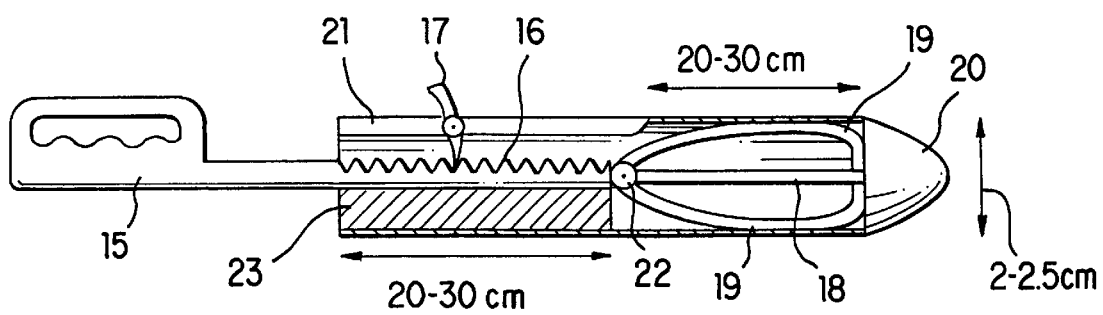
FIG. 5.
Figure 6:
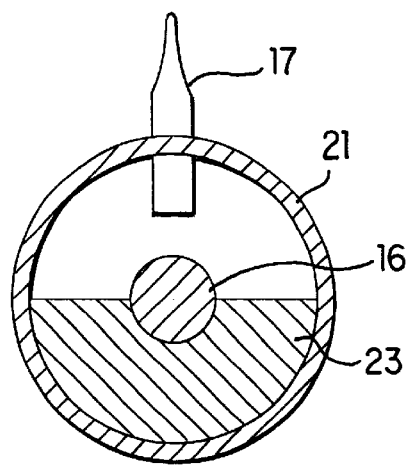
FIG. 6.
Figure 7A:
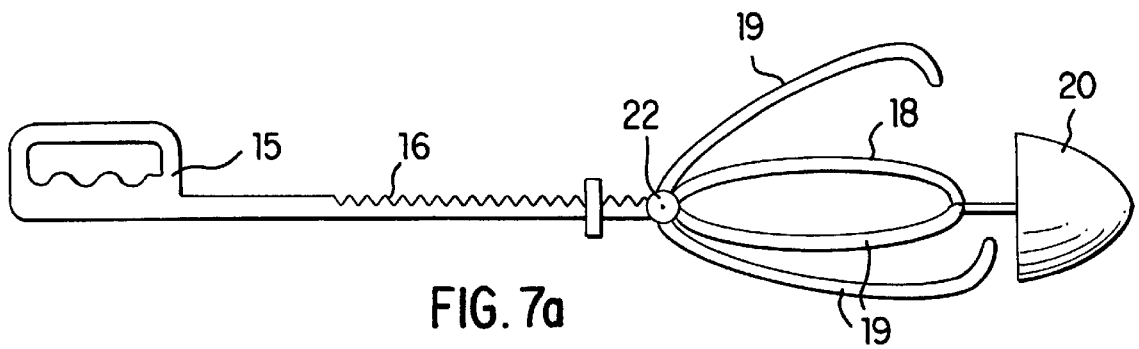
FIGS. 7a–7b.
Figure 7B:
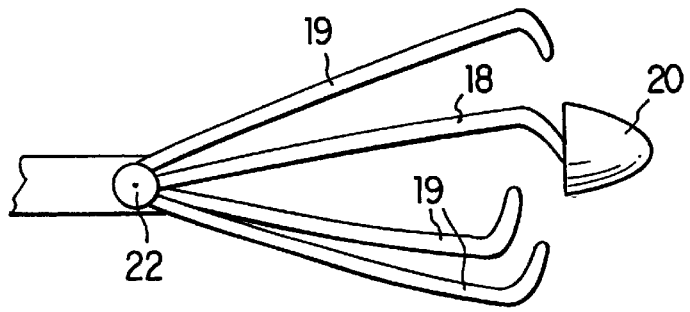

Since the prosthetic device will be surgically implanted into a patient it should be kept in a sterile state prior to use. The device may also be implanted during thorascoscopic surgery with the aide of a deployment device that can be used to help position the prosthesis during surgery and then retracted (see FIGS. 5–7). Standard methods used for manufacturing implantable medical devices and for packaging such devices in a sterile state may be used for all of the components of the invention.

In a preferred embodiment, the device is implanted into a patient that has undergone lung volume reduction surgery (LVRS). During implantation, the sealable ports of the device are positioned either at, or immediately below, the patient's skin. After surgery, the patient should be examined at regular intervals to determine whether improvements resulting from lung resizing are being lost due to a progressive decrease in the elastic recoil of lung tissue. When this occurs, the implanted bladder can be expanded or contracted by means of the sealable port to re-optimize the relationship between the size of the patient's lungs and their pleural cavity. In this manner, the benefits of LVRS can be prolonged.

During surgical implantation, the bladder of the prosthetic device should be positioned between a patient's lungs and their chest wall so that, upon expansion, one side of the bladder pushes against the wall of the pleural cavity and the opposite side makes contact with the patient's lung. Preferably, the surface of the prosthetic device making contact with lung tissue is coated with a solution containing fibrinogen, or fibrinogen with collagen, and the lung itself is coated with thrombin. Upon making contact, a fibrin matrix forms which seals the lung to the prosthetic device helping to prevent any air leaks. By way of example, the surface of the device may be immersed in a solution of 3 mg/ml fibrinogen dissolved in 5 mM Tris buffer (pH 7.5) containing 10 $\mu$g/ml of dipalmitoylphosphatidylcholine. The fibrinogen solution would be allowed to dry to form a coating matrix. A separate solution of 1,000 units/ml of thrombin in 2.5 mM $CaCl_2$(3.3 units of thrombin per mg fibrinogen) may be prepared and applied to the surface of the patient's lungs. The fibrinogen-coated surface of the device may then be applied to the thrombin-coated surface of the lungs to form a crosslinked fibrin matrix.

EXAMPLES

I. Clinical Perspective

Recommended therapies for emphysema have, until recently, been focused primarily on opening narrowed, constricted or clogged airways despite the fact that emphysema is principally a disease of tissue destruction rather than airway narrowing. For example, the American Thoracic Society "step-wise" approach to the treatment of emphysema is strikingly similar to that recommended for the treatment of asthma (ATS statement, *Am. J Resp. Crit. Care Med.* 152:s84–s96 (1995)). Although emphysema, chronic bronchitis and asthma, all cause an obstruction to airflow, exercise limitation, and lung hyperinflation, the physiological bases for these common patterns of lung dysfunction are distinctly different. In asthma and chronic bronchitis, the primary factor limiting airflow is obstruction and narrowing of the conducting airways. In emphysema, the primary factor limiting airflow is destruction of lung tissue and loss of elastic recoil. While conventional medical therapies for chronic obstructive pulmonary disease (COPD) such as bronchodilators, mucolytics, and anti-inflammatories improve lung function in many patients with emphysema, they do so by improving the "asthmatic-bronchitic" component of the disease rather than by affecting the primary physiological abnormality, i.e., the destruction of tissue. Thus, such therapies generally produce, at best, only modest physiological improvements in emphysema.

As a result of the tissue destruction and loss of elastic recoil that characterize emphysema, the pressures which act to push gas out of lungs are reduced. This leads to the trapping of gas within the lung along with hyperinflation and compromised respiratory muscle function. In 1994, Cooper et al. successfully demonstrated that resection of the lung in selected patients with end stage emphysema can be performed safely and effectively using current technologies, and have a dramatic impact on respiratory function and functional capacity (*J. Thorac. Cardiovasc. Surg.* 109:106–119 (1995)). Surgical resection, resulting in "resizing" of the lung relative to the chest wall, causes an improvement in elastic recoil pressures, an increase in vital capacity, and a marked improvement in expiratory flow with minimal morbidity and mortality. This approach, known as "lung volume reduction surgery" (LVRS) has produced similar benefits among over 2,000 patients at medical centers in America, Canada and Europe (Ingenito, et al., *N. Engl J. Med.* 338:1181–1185 (1998); Martinez, et al., *Am. J. Resp. Crit. Care Med.* 155:1984–1990 (1997)) and currently is the focus of a multi-center randomized national trial to assess its impact on quality of life and longevity in the emphysema population. Results today clearly indicate that LVRS produces a marked improvement in lung function among the majority of emphysema patients who receive it and suggest that LVRS represents an important therapeutic option for patients with end stage obstructive lung disease.

II. Physiological Mechanisms of Improvement Following LVRS

Most investigators have quantified improvement in lung function following LVRS in terms of the volume of gas expired within one second, the $FEV_1$, which is a standard method for assessing lung function that can be readily measured in any pulmonary function lab. $FEV_1$ can be thought of as determined by two independent properties of the lung: 1) the impedance to the flow of gas during expiration which determines the rate of lung emptying; and 2) the total amount of gas that can be expired from the lung during expiration, known as the forced vital capacity (FVC), which determines the absolute volume of lung which can empty (Ingenito, et al., *Am. J. Resp. Crit. Care Med.* 157:A497 (1998)). The first of these, the impedance, is directly related to the ratio of the amount of gas that can be expired in one second relative to the amount that can be expired inn total, i.e., $FEV_1/FVC$ ratio. Considering $FEV_1$ as a dependent parameter determined by the product of these independent physiological properties, the $FEV_1$ can be expressed according to the following simple relationship:

$$FEV_1 = (FEV_1/FVC) \times FVC. \qquad 1)$$

The above expression reduces to the identity, $FEV_1 = FEV_1$. Expression (1) can now be utilized to consider how $FEV_1$ might change as a function of changes in impedance to airflow (i.e., the $FEV_1/FVC$ ratio, mechanism I), and/or changes in the effective functional lung volume (mechanism II) following an intervention such as the administration of a medication, or the performance of LVRS. To examine this question, equation 1 must be expanded mathematically in a Taylor series, yielding the following expression:

$$\delta FEV_1 = \underbrace{FVC_{pre}\delta(FEV_1/FVC)}_{\text{Mechanism I}} + \underbrace{(FEV_1/FVC)_{pre}\delta FVC}_{\text{Mechanism II}} \qquad 2)$$

where δ represents the change that occurs in the designated parameter resulting from an intervention (such as medical intervention or volume reduction therapy) and "pre" represents the value of the subscripted parameter prior to the intervention. This simple mathematical expression indicates that the $FEV_1$ can improve either by a change in obstruction to airflow during an expiratory maneuver (mechanism I), or a change in the absolute amount of gas in the lung at the start of the expiratory maneuver (mechanism II).

It was initially hypothesized that LVRS might improve expired gas flow primarily through mechanism I by: 1) increasing tethering of floppy airways as a result of increased tissue recoil and reduced resistance to airflow; and 2) increasing recoil pressures for a given lung volume, thereby producing a greater "push" or driving pressure during the expiration. However, results from patients who have undergone LVRS suggest that the factor primarily responsible for improvement in lung function is not mechanism I, which would occur through an increase in the $FEV_1/FVC$ ratio, but rather mechanism II, in which FVC, the amount of functional lung, increases.

Recent work suggests that LVRS increases FVC by resizing of the lung relative to the chest wall thereby producing a greater reduction in trapped gas or residual volume (RV) than in total lung volume (total lung capacity or TLC) (Fessler, et al., *Am. J. Resp. Crit. Care Med.* 157:715–722 (1998)). Total lung capacity minus residual volume is precisely equal to the functioning volume of the lung, the vital capacity (FVC above). The majority of patients undergoing LVRS experience an increase in vital capacity by virtue of the resizing of compliant lung relative to stiff chest wall. Vital capacity will increase following LVRS as long as lung compliance, the stiffness of the lung, does not decrease too drastically.

While this model provides a clear explanation for why FVC increases in the majority of the patients that undergo LVRS, it also provides a rationale for why some patients who undergo LVRS do not improve lung function. Since clinical studies demonstrate the changes in FVC resulting from lung-chest wall resizing determine most of the physiological improvement following LVRS, surgery which reduces lung volume and causes lung stiffening but fails to increase vital capacity can actually have a detrimental effect on function. After surgery, vital capacity first increases, and then progressively decreases as the extent of tissue resection becomes too great. This occurs despite progressive increases in elastic recoil pressure and decreases in overall lung volume, effects that have traditionally been thought of as beneficial consequences of LVRS. Results suggest that an "optimum tissue resection volume" exists for which vital capacity improves and that overly aggressive resection may actually detract from the beneficial effects of LVRS despite increasing recoil pressure and lung elastance.

Current approaches for determining the extent and location of tissue resection for LVRS are relatively imprecise. Both inadequate tissue resection and overly extensive tissue resection can result in the failure of a given LVRS procedure to produce a physiological benefit. Between these extremes are ranges of responses which vary from optimal to minimal. Unfortunately, once the procedure has been performed, it is difficult, if not impossible, to alter the ultimate response. Repeat LVRS procedures are extremely high risk and are not performed by most surgeons. Medical therapies affect lung function only indirectly, and have no impact on the physiological determinants of response to LVRS. Thus, patients whose response to surgical therapy is sub-optimal as a result of either: 1) an LVRS procedure which is not extensive enough to produce an effective reduction; or 2) an LVRS procedure which is so extensive that excessive lung stiffening and a loss of functioning volume occurs, have been left with few medical options. Moreover, among patients who demonstrate an initially favorable response to LVRS, physiological benefits have tended to wane over time. Results have clearly indicated that improvements which follow LVRS decline by one year postoperatively and, many patients have lost the majority of their initially favorable response by two to three years following surgery (Brenner, et al., Chest 113:652–659 (1998)).

III. Use of Lung Prosthetic Device

The above considerations suggest that an approach which allows for adjustments in lung-chest wall resizing and recoil pressures without requiring additional high risk surgery will be of clear benefit. Such an approach would allow for: 1) short term optimization of response to surgery; and 2) the ability to improve lung physiology long term as the lung undergoes stress relaxation. This can be achieved using an inflatable lung prosthesis which is placed within the thorax during LVRS and positioned between the lung and chest wall. This device is coated with a biocompatible tissue glue on its inner surface such that it adheres to both the visceral pleural surface and assists with the sealing of post-operative air leaks.

The prosthetic device is made of a biocompatible, gas impermeable, flexible material. By changing the volume of gas within the prosthesis, it is possible to adjust intrapleural pressures, lung volume, and the work of breathing. Using physiological measurements of pleural pressure and expiratory flows, the response to LVRS can be optimized at selected time points following surgery. For example, gas can be removed from the prosthesis as lungs undergo stress relaxation and loss of elastic recoil, thereby causing an increase in recoil pressure and an improvement in lung function without additional surgery. The device has the potential to: 1) reduce post-operative morbidity by acting as a surgical "patch" to decrease the incidence of air leaks; 2) optimize short term response to LVRS by allowing for modulation of effective lung resizing once recovery from surgery is complete; and 3) extend the duration of benefit from LVRS by allowing for adjustment in recoil pressures through intermittent removal of gas and lung-chest wall resizing over time.

IV. Physiological Rationale for Lung Prosthesis

An extensive lung volume reduction procedure will be beneficial from the perspective that as the lung undergoes stress relaxation, and RV and TLC increase over time, both would reach pre-operative baseline values after a longer period if the initial resection of diseased tissue is greater. Thus, the potential duration of benefit following an extensive procedure could be greater than that following a more limited procedure. A more extensive procedure also has the benefits of reducing FRC and decreasing the work of breathing by allowing chest wall recoil to contribute to passive expiration. Two factors alter this rather simple view of the effects of volume reduction on lung physiology: 1) an initial procedure which is too extensive can adversely affect lung function by causing a reduction in vital capacity; and 2) the rate of decline in lung function following LVRS is proportional to the degree of increase in recoil pressure, and thus, lung function declines faster following a more extensive procedure compared to a less extensive procedure (Ingenito, et al., Am. J. Resp. Crit. Care Med. 157:A497 (1998)).

For the reasons discussed above, the ability to adjust intrapleural pressures and relative lung-chest wall volumes post-operatively will be very desirable. The lung prosthesis provides a mechanism for performing such adjustments with the primary objective of prolonging the duration of benefit from lung volume reduction therapy. For example, a patient who undergoes a conventional lung volume reduction procedure with a significant improvement in vital capacity may show an initial favorable response. Over time, this benefit will decline and, after a period of two to three years, the patient may be in essentially the same state as prior to surgery. A more aggressive volume reduction procedure may produce greater benefits initially but, since recoil pressures will be correspondingly increased, stress relaxation towards a pre-operative state will occur in a correspondingly more rapid fashion. Thus, the benefits of the additional resection after two years will be of little clinical utility. If the benefits of this additional tissue resection could be "captured" and released over time, however, then the more extensive procedure would serve to prolong the duration of benefit from LVRS. This is where the LVRS prosthesis is of maximum potential benefit.

The pressure-volume relationship of the lung is nonlinear, especially at high lung volumes. It can be described by the exponential relationship:

$$V(P) = V\text{max} - [V\text{max} - V\text{min}]\, e^{-kP}$$

where V is volume, P is pressure, Vmax and Vmin are the maximum and minimum volumes that the lung can achieve, and k is a constant that determines the shape of the exponential. The nonlinear shape of the P-V relationship of the lung is determined by the collagen-elastin fiber network within the tissue which, in emphysema, is abnormal. These abnormalities in tissue structure are responsible for determining the increased Vmax and Vmin, and decreased k values characteristic of emphysema patients. In this patient population, however, they serve to allow the LVR prosthesis to function better than in a patient with a more normal P-V exponential relationship. The inflation volume of the prosthesis ($\Delta V_T$) in part causes a slight deflation of the lung ($\Delta V_L$) and a slight inflation of the chest wall ($\Delta V_{CW}$). The relative changes in chest wall size and lung size are dictated by their relative elastances. Given the stiffness of the lung, at or near full inflation, the prosthesis volume should contribute about equally to $\Delta V_L$ and $\Delta V_{CW}$. Inflating the prosthesis will decrease TLC to a small degree, but have little effect on lung volumes at low distending pressures. Thus, RV should be minimally affected, if at all. Prosthesis inflation will tend to cause a decreased VC, but, given the nonlinear characteristic of the P-V relationship, this decrease will be very small since small changes in volume are associated with large changes in recoil pressures which determine the rate of stress relaxation over time. By either inflating or deflating the prosthesis, as guided by physiological measurement of transpulmonary pressures, lung volumes, and lung resistance and compliance, lung function can be optimized at a given point and time and followed serially to ensure that recoil pressures are not causing an accelerated rate of lung function over time.

Eventually, even with the use of the prosthesis, the LVRS lung is expected to undergo spontaneous stress relaxation with a loss of elastic recoil and a progressive increase in lung compliance. As stress relaxation occurs, total lung capacity and residual volume will increase, compliance will increase, and vital capacity will decrease. Balloon deflation allows the lung to expand and resize to the chest wall, resulting in an increase in TLC and an increase in vital capacity with little detrimental effect on RV. The physiological basis for improvement in vital capacity in this instance resides in the fact that prosthesis deflation increases transpulmonary distending pressure which tends to maintain alveolar patency during expiration and increase TLC relative to a fixed RV, improving vital capacity. Thus, over time, deflation of the prosthesis can be used to compensate for lung stress relaxation and improve lung function without any surgical or medical interventions.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A prosthetic device for implantation into the pleural cavity of a patient, comprising:
   (a) a bladder made of a biocompatible gas-impermeable, elastomeric material, said bladder comprising two chambers:
      i) an inner chamber formed by the lumen of multiple, inflatable septated compartments, wherein said septated compartments are made of biocompatible gas-impermeable, elastomeric material and are interconnected to allow the exchange of gas; and
      ii) an outer chamber, external to said septated compartments and internal to the inner surface of said bladder;
   (b) a connector tube made of biocompatible, gas-impermeable, elastomeric material, wherein:
      i) said connector tube has two separate passageways for gas, one to said inner chamber and one to said outer chamber, each passageway terminating at the proximal end of the connector tube in a port with a self sealing membrane; and
      ii) said connector tube has a distal end attached to said bladder.

2. The prosthetic device of claim 1, wherein said bladder is 20–40 cm in diameter, each of said septated compartments is 1–2 cm in diameter, and said connector tube is 10–20 cm in length.

3. The prosthetic device of either claim 1 or claim 2, wherein said bladder has multiple distinct lobes.

4. The prosthetic device of claim 1, wherein said bladder and said connector tube are made of a material selected from the group consisting of: silicone rubber; polypropylene and polyurethane.

5. The prosthetic device of claim 1, further comprising an oscillating pump which is connected to the passageway leading to said outer chamber and which provides a means for reciprocally expanding and contracting said bladder.

6. The prosthetic device of claim 1, further comprising a deployment device that can be used to aid in the surgical implantation of said prosthetic device.

7. A method of treating a patient for emphysema or respiratory failure, comprising surgically implanting the prosthetic device of claim 1 into the pleural cavity of said patient between the chest wall and lungs, wherein said the ports at the distal end of the connector tube are positioned at the surface of, or immediately below, the skin of said patient and provide a means for externally adjusting the volume occupied by said bladder.

8. The method of claim 7, wherein said prosthetic device is implanted after or during lung volume reduction surgery on said patient.

9. The method of either claim 7 or 8, wherein, after the surgical implantation of said prosthetic devise, gas is introduced or removed from the inner chamber of said bladder in order to optimize the lung recoil of said patient.

10. The method of claim 8, further comprising directly attaching said prosthetic device to the visceral pleural surface of said patient's lung by:
    a) coating said visceral pleural surface with thrombin;
    b) coating the surface of said prosthetic device that contacts said patient's lung with fibrinogen or a fibrinogen/collagen mixture; and
    c) contacting the thrombin-coated visceral pleural surface of said lung with the fibrinogen-coated surface of said prosthetic device so that a fibrin matrix forms which holds these surfaces together.

11. A method for providing respiratory assistance to a patient, comprising:
    a) surgically implanting the prosthetic device of claim 1 into the pleural cavity of said patient;
    b) attaching said connector tube to an oscillating pump by the port leading to the outer chamber of said bladder; and
    c) using said pump to reciprocally inflate and deflate the bladder of said prosthetic device.

* * * * *